US006656735B1

(12) United States Patent
Wurst et al.

(10) Patent No.: US 6,656,735 B1
(45) Date of Patent: Dec. 2, 2003

(54) METHOD FOR IDENTIFICATION OF TARGET GENES OF TRANSCRIPTION FACTORS

(75) Inventors: Wolfgang Wurst, München (DE); Alain Prochiantz, Paris (FR)

(73) Assignees: GSF Forschungszentrum Fuer Umwelt Und Gesundheit GmbH, Oberschleissheim (DE); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/152,361

(22) Filed: Sep. 14, 1998

(30) Foreign Application Priority Data

Sep. 15, 1997 (DE) .......................... 197 40 578

(51) Int. Cl.[7] .......................... C12Q 1/68; C12N 15/63; C12N 15/87; C12N 15/00; C07H 21/04
(52) U.S. Cl. ..................... 435/463; 435/320.1; 435/455; 435/6; 536/23.1; 536/23.5; 530/350
(58) Field of Search ............................ 435/6, 455, 458, 435/461, 320.1, 463; 536/23.1, 23.5; 530/350

(56) References Cited

U.S. PATENT DOCUMENTS 5,364,783 A * 11/1994 Ruley et al. ............. 435/235.1
5,627,058 A    5/1997 Ruley et al.
5,922,601 A *  7/1999 Baerscher et al. ......... 435/456

OTHER PUBLICATIONS

Derossi et al., Cell Internalization of the Third Helix of the Antennapeida Homeodomain Is Receptor–independent, Jul. 26, 1996, The Journal of Biological Chemistry, vol. 271, No. 30, pp. 18188–18193.*
Joliott et al., Antennapedia homeobox peptide regulates neural morphogenesis, Mar. 1991, Proc. Natl. Acad. Sci. USA, vol. 88, pp. 1864–1868.*
Derossi et al., The Third Helix of the Antennapedia Homeodomain Translocates through Biological Membranes, Apr. 1994, vol. 269 No. 14, The Journal of Boilogical Chemistry, pp. 1044–10450.*
Camus et al., Molecular Reproduction and Development 45:255–263, 1996.*
Kang et al., Mol. Cells, vol., 7 (4), p. 502–508, Aug. 31, 1997.*
Tenen et al., Blood, vol. 90 (2), p. 489–519, Jul. 15, 1997.*
Forrester, et al. "An Induction Gene Trap Screen in Embryonic Stem Cells: Identification of Genes that Respond to Retinoic Acid" *Proc. Natl. Acad. Sci. USA* (Feb. 1996) vol. 93, pp. 1677–1682.
Gogos, et al. "Selection for Retroviral Insertions into Regulated Genes" *J. of Virology* (1997) vol. 71(2), 1644–1650.
Harrison, et al. "Functional Identification of Genes Up– and Down– Regulated by Glucocorticoids in AtT–20 Pituitary Cells Using an Enhancer Trap" *Endocrinology* (Jul. 1996) vol. 137(7), pp. 2758–2765.
Hill, et al. "Screening for Novel Pattern Formation Genes Using Gene Trap Approaches" *Methods in Enzymology* (1993) vol. 225, pp. 664–681.
Mainguy, et al. "Regulation of Epidermal Bullous Pemphigoid Antigen 1 (BPAG 1) Synthesis by Homeoprotein Transcription Factors" *J. of Investigative Dermatology* (Oct. 1999) vol. 113, pp. 643–650.
Mainguy, et al. "An Induction Gene Trap for Identifying a Homeoprotein—Regulated Locus" *Nature Genetics* (Jun. 2000) vol. 18, pp. 746–749.
Russ, et al. "Identification of Genes Induced by Factor Deprivation in Hematopoietic Cells Undergoing Apoptosis Using Gene–trap Mutagenesis and Site Recombination" *Proc. Natl. Acad. Sci. USA* (Dec. 1996) vol. 93, pp. 15279–15284.

* cited by examiner

*Primary Examiner*—Shin-Lin Chen
(74) *Attorney, Agent, or Firm*—Townsend & Townsend and Crew LLP

(57) ABSTRACT

Transcription factor responsive elements, target genes, and co-factors of a transcription factor, either individually or in combination, are identified by integrating into the genome of a eukaryotic cell a gene trap vector that includes a reporter gene, a polyadenylation site, and a selectable marker gene, selecting the cells in which the gene trap vector is successfully integrated and contacting those cells with the transcription factor, then identifying and cultivating those cells having a gene into which the gene trap vector has been integrated and in which the reporter gene activity has been altered by interaction between the transcription factor and a transcription factor responsive element of that gene, and identifying the transcription factor responsive element, target gene, or cofactor that interacts with the transcription factor.

15 Claims, 10 Drawing Sheets

(2 of 10 Drawing Sheet(s) Filed in Color)

tgctggacccagccgagagggctgtgcttcgga-
tagcagatgagcgggacaaagttcaaaagaaaa-
catttacaaaatggataaatcagcatctcat-
gaagggtcccaggtcccgaaaaccaaagaagaa-
gaaccctaacaaagaggacaagcggcctcgca-
cagccttcactgctgagcagctccagaggct-
caaggctgagtttcagaccaacaggtcgacaa

PC12 cells

EnHD

− +

BPAG1n

GAPDH

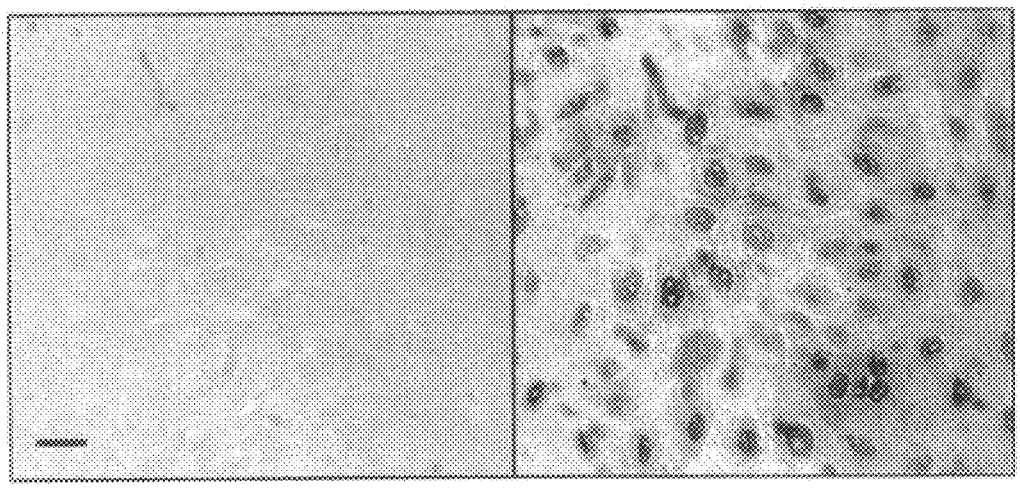
FIG. 5A
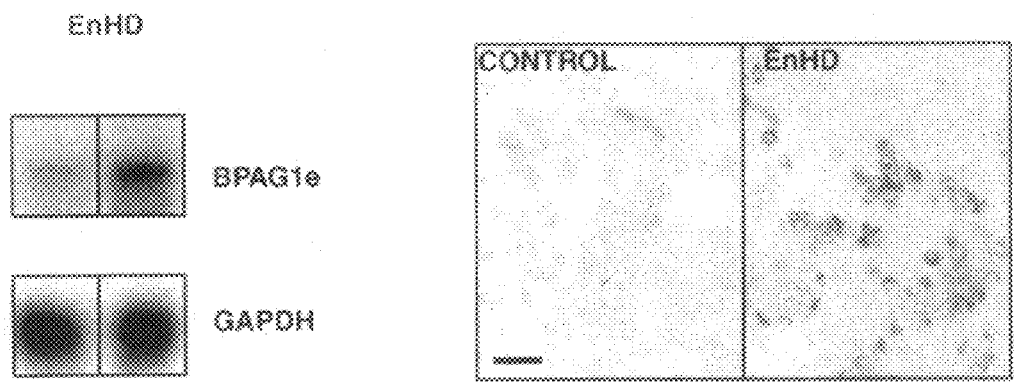
FIG. 5B
FIG. 5C
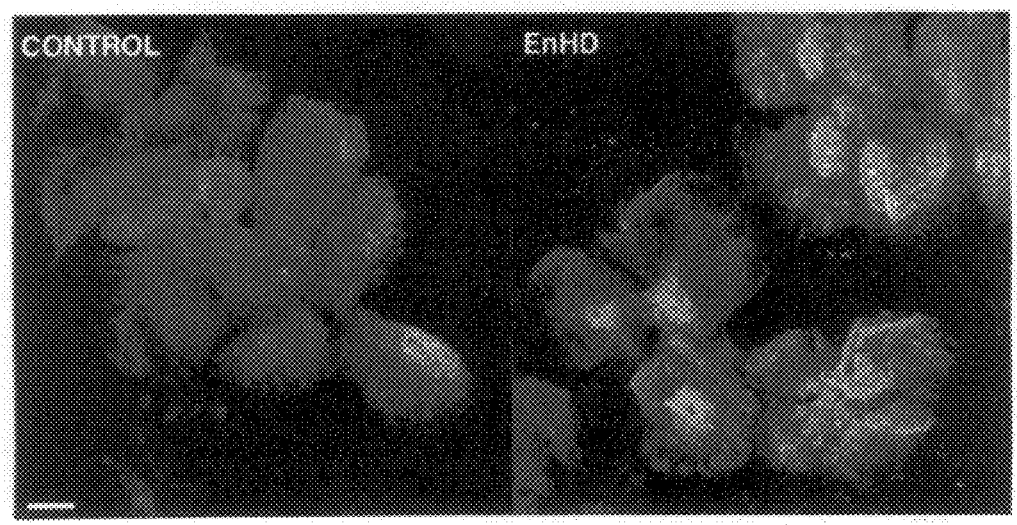
FIG. 5D

FIG. 6A
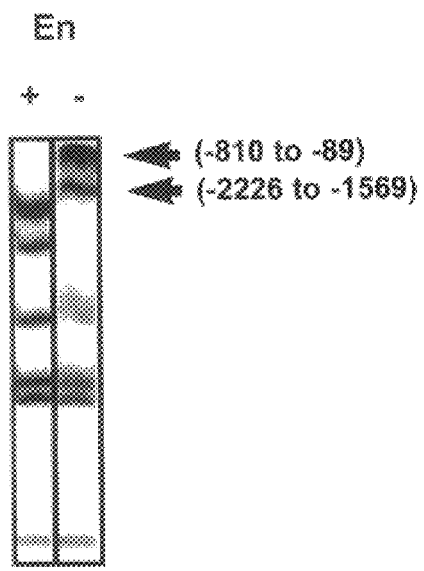
FIG. 6B
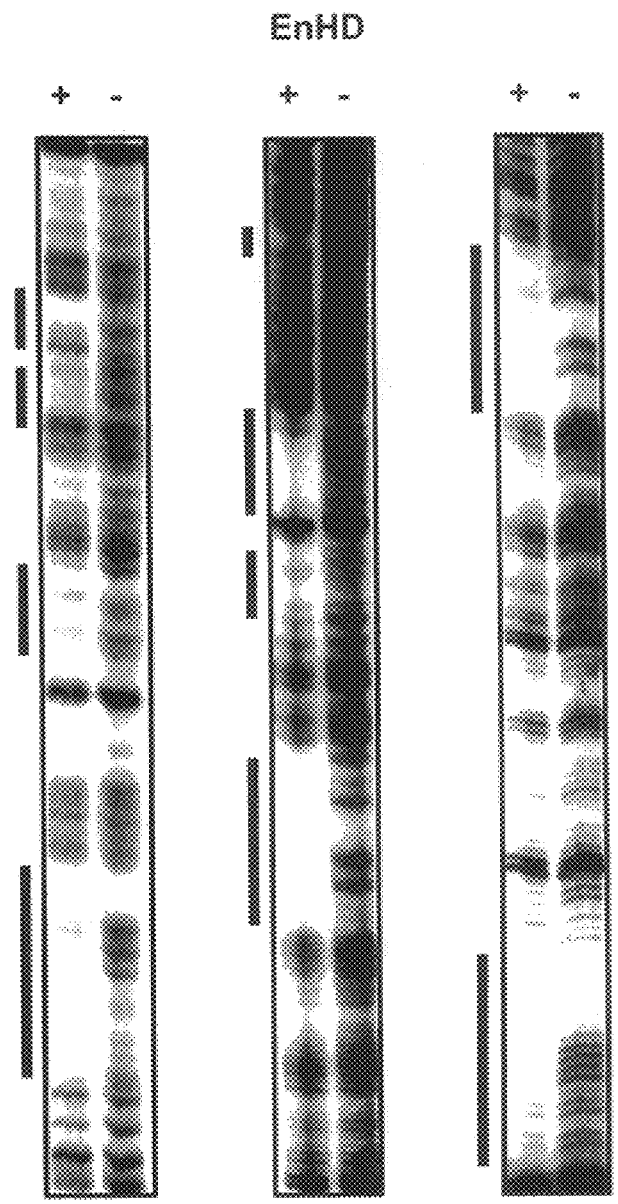
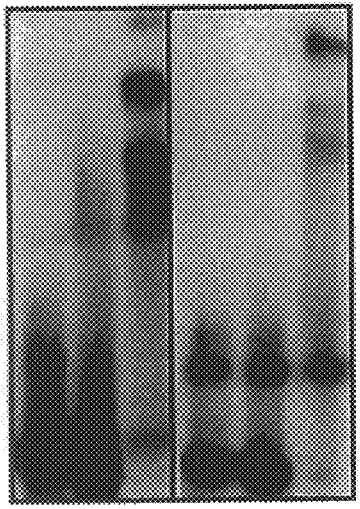
FIG. 6C (-1569)

ctgaattgcaacctgccctgcccctgtttagcttcccagtactgggctta
cagtagacttgcactg taacacaagcctagatgatataaacttctttt gtg
atatgtatgcagtcgtaacaatacaaa gttgattatgatgcacattaaa
attctgatactgctgtagtgaccaaactatcttttcttggtg tctttaattc
aaatggctcatttaatgtcttcattt taactacctgtaaggctgcacccta
agcatttacagttcatttagttcatagctgctgctgtagacatggtaact
ttatgagttaacaaggatgtcagccagtaatatatcttaattcatggcct
ttgcattcataatgtaatatatattatctttaattacttccattccatggcaaca
ctgaagtcggtgtcaagacagtgaggacagcagctacactgcgtgtctct
gttttgtcttggcattggagcaaggcactggtaaggaccaagtggcttaa
gctcctctacattctcagagcgaattctcagaggtaacaagtggcttaaac
actccatgaagaaatgaaattataaccaaggaagaaccctgaac
aatactcaaataattagtcattaaaaaaataaaagg catatgagcca
gcctgg (-2226)

(-89)

cttaaatatgctgtggcgtgatatgcaatgcactgcaaatactgctgataact
attctaaagaatcctgcctacagcatcatttgctgctgagttgcctttgta
gccagcattaaagccctgcaag tacgggcagagcaggacgattgggcgt
cactgggaaagatatgccaaatatttcaccaaga gtcatccagcttcaac
cacctaaaaaacaactcaggtacacaggagcccggcagcac cagtgaa
ggtaatgctcatcaataccaagcaccaaccagaacacacaagctcagatcac
acagctgacaaatgctggactaatcagcaagcagatcccacgtgcttcctaacac
aaggtaaaatgctggactaatcagtcaataagtcaataataatcatcaagca
cacaaattaatgagaaaccaaaatctgtttcatttgaccatctctccattgt
tcaccgcattaaaattaactgaaaaatgttcaattacttttcttgtgata
aactctctccaagccactgtttggattctaaagccaaagactcca cg
cagaaatattggctcagtaactaagtgtgaatgtg tctgggcttgctcttctt
cacagagactag (-810)

FIG. 6D

METHOD FOR IDENTIFICATION OF TARGET GENES OF TRANSCRIPTION FACTORS

BACKGROUND OF THE INVENTION

1. Field of the Invention

The present invention relates to a methodefor identification of transcription factor responsive elements, target genes and/or co-factors of transcription factors.

2. Description of the Prior Art

Among the numerous genes that control metazoan development, homeogenes play a key role in cell lineage decisions and in establishing the morphological identity of multicellular domains. They are expressed in all tissue layers of the organism and at different stages during development. They code for homeoproteins, a large family of transcription factors characterized by a highly conserved 60 amino-acids DNA-binding domain, the homeodomain.

The mammalian Engrailed homeoproteins, Engrailed-1 and Engrailed-2 (En1 and En2) are expressed first in the anterior neuroepithelium at the 1 somite—(in the case of En1) and 5 somite—(in the case of En2) stages in a domain, which will later develop into midbrain-hindbrain territory. Then, En1 is expressed in the spinal chord, in the dermomyotome of the somites and the ventral ectoderm of the limb bud. Gene inactivation experiments showed, that En1 is necessary for the development of mid/hindbrain, the sternum and the ventral limb bud, whereas En2 mutants only display a slight mid/hindbrain patterning phenotype.

However, gene replacement experiments of En1 by En2 suggest, that both proteins have identical biochemical properties and that the different phenotypes in brain development observed in En1 and En2 mutants are due to temporal differences in the expression of both genes during early neurogenesis. Therefore, in this study En1 and En2 are often summarized and referred to as Engrailed.

As illustrated in the case of Engrailed, analysis of expression patterns and of the morphological modifications which were produced in murine embryos mutated for distinct homeogenes, have been invaluable to understand the function of these homeogenes during development. However, the understanding of their precise mode of action requires the identification of the genetic networks executing their functions. Considering the Engrailed mutant phenotypes potential targets might be involved in tissue patterning (secreted molecules), in cell type specification (other transcription factors), in cell migration (cell and substrate adhesion molecules) and in cell morphogenesis (structural proteins.

In Drosophila, genetic approaches unraveling functional interactions in mutants and the search of DNA-binding sites in polytene chromosomes have been available to screen for target genes of any given transcription factor. The application of these techniques led to the identification of a number of putative engrailed target genes, such as hedgehog, decapentaplegic, cubitus-interrupus (ci), polyhometic and β3-tubulin. Only ci and β3-tubulin were shown to be direct target genes of engrailed. The genetic methods used in the fruit fly and which in principle might give access to such genetic pathways are not easily applicable to vertebrates due to the very high number of offsprings that would have to be screened, and to the inavailability of polytene chromosomes. In vertebrates, most putative homeoprotein target genes have either been discovered fortuitously by promoter analysis or by homology with genes already identified in the invertebrates, primarily in Drosophila. In most cases, the evidence that the identified genes are true target genes has remained rather circumstantial. It is particularly noteworthy that, with some exceptions illustrated by a recent study on NCAM, almost none of these target genes have been shown to be regulated by homeoproteins in vivo.

SUMMARY OF THE INVENTION

It is an object of the present invention to provide a method for the identification of transcription factor responsive elements, target genes and/or co-factors of transcription factors, said method enabling a systematic determination of these elements, target genes and co-factors and avoiding the disadvantages known from the prior art.

This object is achieved according to the present invention by means of a method for identification of transcription factor responsive elements, target genes and/or co-factors of transcription factors with the following steps of:

(a) introduction of a gene trap vector into a eukaryotic cell in culture, wherein said gene trap vector exhibits at least the following elements in functional arrangement:
   a reporter gene
   a polyadenylation site
   a selectable marker gene (b) selection of cells containing the vector;

(c) contacting the selected cells with a transcription factor, the corresponding transcription factor responsive element, target gene and/or corresponding co-factor of which is to be analyzed;

(d) identifying and cultivating such cells, which show an alteration of the reporter gene activity;

(e) identifying the target genes and/or co-factors of the transcription factors and/or the transcription factor responsive elements.

BRIEF DESCRIPTION OF THE DRAWINGS

The file of this patent contains at least one drawing executed in color. Copies of this patent with color drawings are provided to the Patent and Trademark Office with payment of the necessary fee.

FIGS. 5A, 5B, 5C and 5D are representations of the levels of particular proteins expressed in keratinocytes under various conditions, respectively, as further illustrations of the invention.

FIGS. 6A, 6B, and 6C are a mobility shift assay, a DNase footprint analysis, and a gel shift analysis, respectively, of proteins expressed in procedures used to illustrate the invention. FIG. 6D is a nucleotide sequence of a promoter used in an illustration of the invention.

DESCRIPTION OF THE PREFERRED EMBODIMENTS

Figure 1A:
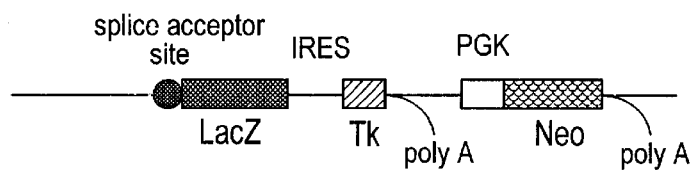
FIG. 1 is an illustration of a cloning strategy used to illustrate the invention.

Gene trap vectors are known per se and have been described e.g. in Hill and Wurst, 1993a and Hill and Wurst, 1993b. These publications are referred to in their entirety.

The gene trap vectors which may be used according to the present invention contain at least a reporter gene, a polyadenylation site and a selection marker gene being arranged in operable linkage.

The transcription of the reporter gene is then modified following integration of the gene trap vector into the genome of a eukaryotic cell, if said reporter gene after addition of a transcription factor is under the control of a transcription factor responsive element. According to the present invention, modification is meant to be an induction or repression of the transcription of the reporter gene, i.e. an increase or decrease of the transcription rate. As a reporter gene, any genes may be used, which may be detected in eukaryotic cells. For example, such genes are LacZ gene, luciferase gene, green fluorescence protein gene and CAT gene. Other suitable reporter genes are known to the persons skilled in the art, which are selected depending on the target cell and on the transcription factor to be tested.

Furthermore, for expression a polyadenylation site is required, which is operably linked to the reporter gene and optionally further genes arranged on the vector.

To identify those cells, which after introduction of the gene trap vector contain said gene trap vector in integrated form, additionally a selectable marker gene is introduced. The selectable marker gene may be any gene selectable in eukaryotic cells, e.g. an antibiotic resistance gene, for example a neomycin or hygromycin resistance gene.

On the gene trap vector, a promoter for the selectable marker gene may be arranged, said promoter being active in the selected target cell. Possible promoters are the phospho glycerate kinase promoter, cytomegalo virus promoter or the β actin promoter.

In a further embodiment of the present invention a fusion protein is formed between the reporter gene and the resistance marker gene; in these cases neither the resistance marker gene nor the selection marker gene carries an own promoter. Instead, following integration into a gene expressed in target cells the expression of the corresponding gene products is controlled by cellular promoters.

By the use of a gene trap vector, which doesn't carry its own promoter for the reporter gene and the resistance marker gene, integrations into active genes may be identified. For example, such a vector contains a splice acceptor site, the reporter gene, the resistance marker gene and a polyadenylation site. An example for the marker gene is the lacZ gene, one instance for the resistance gene is the neomycin resistance gene.

The introduction of the gene trap vector into the target cell is accomplished by any method known from the prior art. These are exemplified by transfection methods, lipofection methods, electroporation and methods using retroviral vectors.

The gene trap vector may contain further genes, regulation and control sequences etc. so as to ensure the expression of the genes present on the vector, and the integration into the genome of the target cell as well as the replication thereof. In detail, reference is made to the literature of Hill and Wurst, 1993a and Hill and Wurst, 1993b mentioned above.

The gene trap vector is introduced into a target cell, the selection of said target cell being dependent on the tranSCRIPTion factor responsible element to be investigated, the target gene of the trascription factor to be investigated and the co-factor of the transcription factor to be investigated. For example, preferred target cells are embryonic stem cell lines, fibroblast cell lines, neuronal cell lines, tumor cell lines and yeast cells.

The introduction of the gene trap vector into an embryonic stem cell line is advantageous in being employable for the creation of chimeric mammals. By crossing such chimeras with wild type animals the mutation caused by the integration may be transferred to the next generation. Thereby, besides identification of a target gene the function thereof may be studied in the entire organism.

Following introduction of the gene trap vector into the eukaryotic cells, said cells are maintained under selection conditions, to select for those cells containing the gene trap vector in an integrated form. In a preferred embodiment of the present invention, the gene trap vector additionally contains a reporter gene for negative selection, e.g. to select for integrations into constitutively active genes. For example, as a reporter gene thymidine kinase gene, diphteria gene or HAT gene is inserted into the gene trap vector. In the use of the thymidine kinase gene as a reporter gene for the selection against integrations into constitutively active genes, the cells are exposed to ganciclovir. Thereby, cells expressing thymidine kinase are switched off.

In the next step of process following selection for cells containing the vector, the cells are contacted with a transcription factor. Said transcription factor is either added to the cell culture medium, or the gene encoding the transcription factor is present on a plasmid in the cell, either in an integrated or non-integrated form, and is under the control of an inducible promoter.

If the transcription factor is added to the cell culture medium, it must be able to cross the cell membrane, so as to enter the cell nucleus. In a particularly preferred embodiment of the present invention, the transcription factor contains a homeodomain enabling said transcription factor to penetrate the cell membrane. In particular, the third helix of homeoproteins is suitable therefor. The domain comprises 60 amino-acids, and is detailed in the following. Of course, further domains may be employed, which enable the protein to cross the cell membrane. If the transcription factor to be investigated does not contain sequences, which enable it to cross the cell membrane, said sequences may be attached to the transcription factor protein at a suitable site.

For example, the gene encoding the transcription factor gene is selected from the group comprising zinc finger genes, pou genes, homeobox-containing genes, HGM-box-containing genes or winged helix genes.

If the gene trap vector has been inserted into a gene, being under the control of a transcription factor rlesponsive element the reporter gene present on the gene trap vector will be expressed following addition and binding of the transcription factor to said element. The expression of the reporter gene may be detected in a manner known per se. In the case of the reporter gene being LacZ gene, as described in Hill and Wurst, 1993, it is stained for β-galactosidase activity. The detection of the reporter genes used is known from the prior art.

Those cells showing an alteration of the reporter gene activity are identified and cultivated. Then, by means of methods known per se, the target genes of the transcription factors, the co-factors of the transcription factors or the transcription factor responsive elements may be identified and analyzed.

In the following, the method according to the present invention is exemplarily shown with rerference to the identification of genes in the genetic regulation pathway of mammalian homeobox genes. In this respect an induction gene trap approach in embryonic stem cells (ES) is combined with the translocation of homeopeptides over biological membranes. This embodiment of the invention makes use of the fact, that different homeodomains and homeoproteins translocate via the cell membrane, when they are added to the culture medium, to eventually enter the nucleus. There, they may regulate the transcription of a reporter gene under the control of a homeoprotein responsive element, which may result in a modulation of the neurite growth.

The subsequent processes in the cell require the specific DNA binding properties of an internalized homeodomain to be maintained; this shows, that the translocated homeodomains interact with the transcription activity of the endogenous homeoproteins, and thus, are suitable for the identification of genes being under the control of the homeoproteins. By the use of an exogenously added homeodomain as an inductor for screening a library with gene trap integrations in embryonic stem cells (ES), genes in the genetic regulation pathway of homeoproteins, including direct homeoprotein target genes, may thus be identified. Since En2 is expressed in undifferentiated ES cells, this novel powerful induction gene trap technology may be illustratively employed with ES cells to search for target genes, which are active in the genetic regulation pathway of Engrailed. By the use of the En2 hcmeodomain (EnHD) as a chemical inductor, we have screened, 30,000 gene trap integrations and identified the dt/BPAG1 locus as a target of Engrailed proteins.

The accompanying figures serve to further illustrate the invention. The figures show:

FIG. 1: Illustration of the cloning strategy.
(A) PT2 vector having its splice acceptor site in front of LacZ, the internal ribosomal entry site (IRES) in front of the thymidine kinase (tk) cDNA, which allows for negative selection in ganciclovir and positive selection of the NeoR (Neo) gene under the control of the phosphoglycerate kinase (PGK) promoter.
(B) In this scheme, the homeodomain of Engrailed (EnHD) translocates across the cell membrane (step 1) and is directed into the nucleus (step 2), where it binds to available sites and competes with endogenous factors, in this case Engrailed (En). It is assumed, that said method favors the specifity of the interaction, since the chromatin structure is perturbed to a minimum.
(C) 30,000 ES cell clones were established following electroporation of linearized PT2 vector and double selection. The resistant colonies were replicated on polyester membranes. EnHD is added to the culture medium containing the membranes, stained for β-gal activity, and blue colonies are picked from the master plate. Following conformation of induction in three independent analyses, positive clones are amplified and the putative targets are cloned by means of 5'-RACE. Out of 30,000 clones 20 have been found to react in the polyester replica assay and 8 were confirmed in the three subsequent independent induction in microtiter wells.

Figures 2A, 2B:
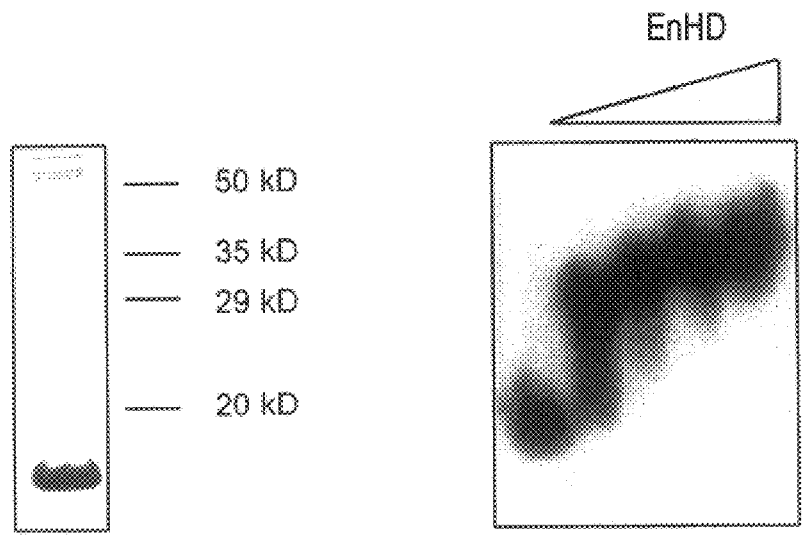
FIGS. 2A, 2B, and 2C are the results of a gel electrophoresis procedure, a band shift assay, and confocal sections, respectively, of cells in culture used to illustrate the invention.
Figure 2C:
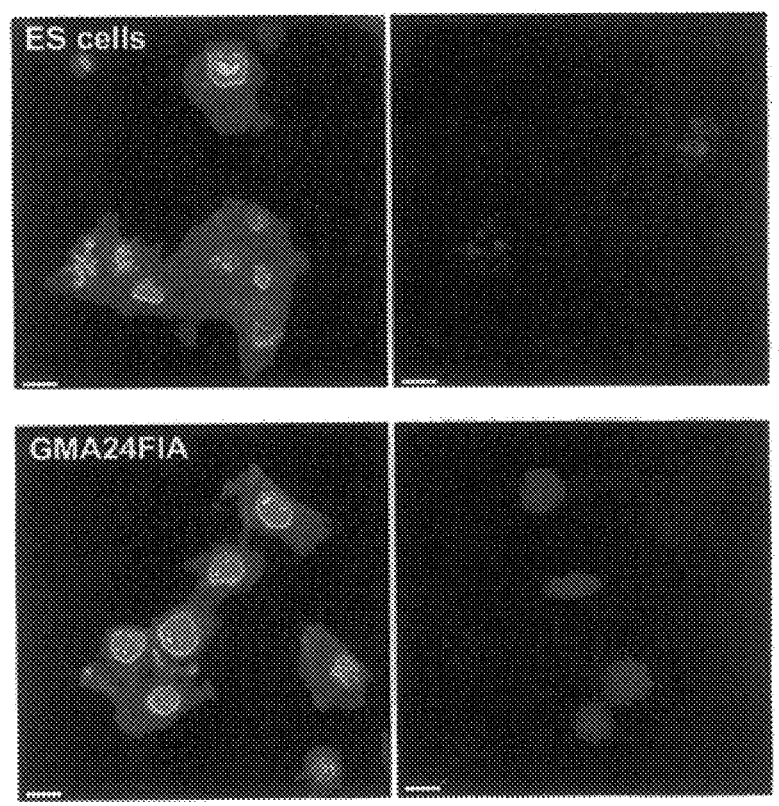

FIGS. 2A, 2B and 2C: Bacterially produced EnHD binds DNA and is efficiently internalized into cells in culture.
(A) Polyacrylamide gel electrophoresis is of EnHD purified from *E. coli* extracts (Coomassie staining).
(B) Band shift assay, performed by incubating 0.5 ng $^{32}$P-ATP-labeled NP6 oligonucleotides with increasing amounts (0, 10, 20, 50 and 100 ng) of purified EnHD.
(C) ES cells (upper Pannels) or GMA24FIA (lower Pannels) were incubated for 2 hrs. with FITC-EnHD (300 ng/ml) (left) or FITC alone (right). Confocal sections show that FITC-EnHD is internalized and accumulates in the nuclei. bar=5 $\mu$m.

Figures 3A, 3B:
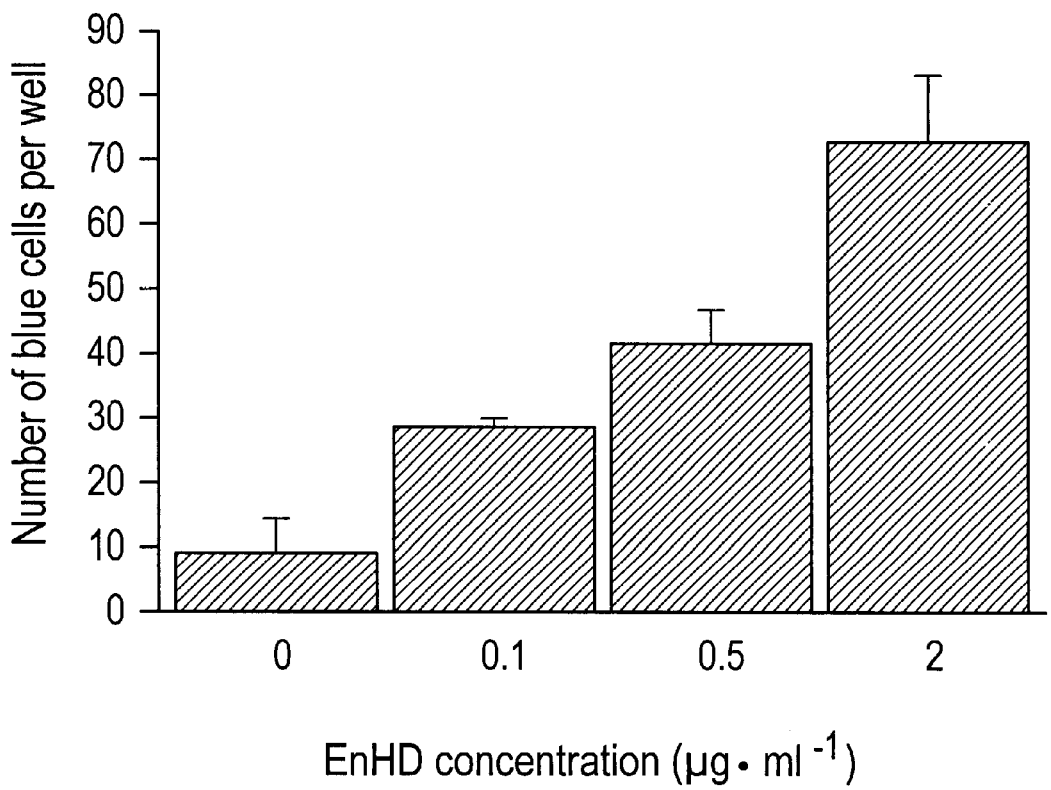
FIGS. 3A, 3B, and 3C are a bar graph, a nucleotide sequence, and genome maps, respectively, used to illustrate the invention.
Figure 3C:
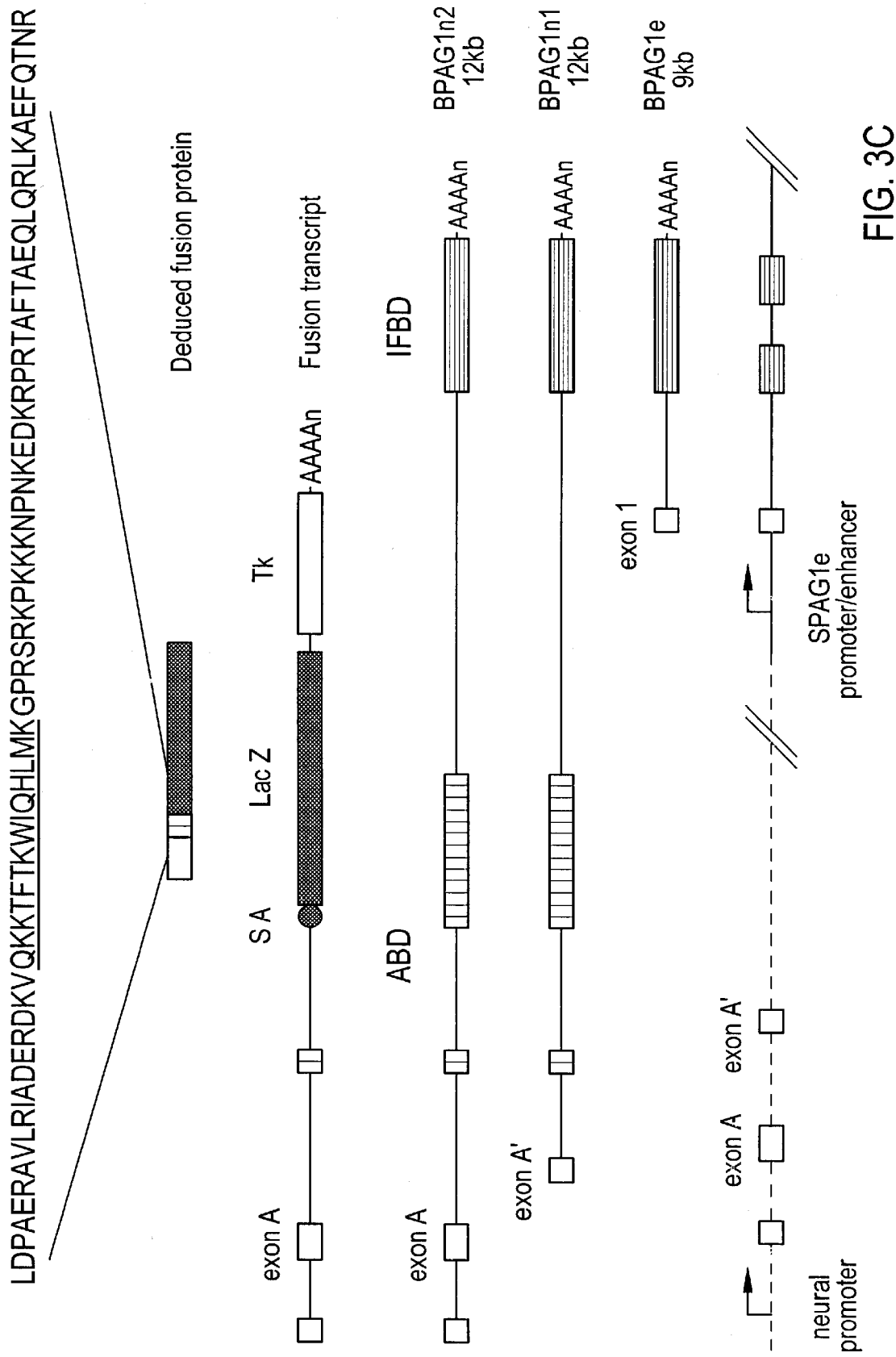

FIGS. 3A, 3B and 3C: Identification of the trapped gene as dt/BPAG1 locus.
(A) 10,000 ES-C3 cells per well were incubated with increasing concentrations of EnHD. After 24 hrs. of incubation, the C3 cells were fixed and stained for β-galactosidase activity. Each column represents the average of 4 independent wells.
(B) 5'-RAC of ES-C3 mRNA revealed the cloning of 225 nucleotides (SEQ ID NO:22) of a BPAG1n2-EnLacZ hybrid CDNA; 56 nucleotides of exon A, followed by 45 nucleotides of the actin binding domain (ABD, underlined) and fused to the splice acceptor site of the vector (bold).
(C) The dt/BPAG1 locus. encodes three transcripts controlled by (at least) two promoters. Two neural specific isoforms, BPAG12n1 and BPAG1n2, have an ABD (hatched box) and an intermediary filament bindung domain (IFBD) (horizontal bars). The BPAG1e isoform is driven by an internal promoter and lacks the ABD domain. The genomic region coding for the ABD comprises at least 100 kb and its exon/intron organization is unknown to a great extend. From the sequence of the hybrid transcript we deduced the structure of the fusion proteins (SEQ ID NO:23): beyond the BPAG1n2-specific C-terminus are 15 amino-acids of the ABD (underlined) in frame with a EnLacZ sequence (bold). The. integration site is believed to be in the first intron of the ABD.

Figure 4:
FIG. 4 is a Northern blot analysis illustrating the invention.
Figure 4:

FIG. 4: EnHD controls BPAG1n mRNA levels in PC12 cells.
(A) After three days of priming with NGF (50 ng/ml) the PC12 cells were incubated overnight with EnHD (300 ng/$10^5$ cells) in the presence of cycloheximide. The BPAG1n transcripts were identified by means of Northern blot analysis with an actin binding domain probe. A 12 kb transcript was detected, the expression of which was decreased by the addition of EnHD, whereas GAPDH expression remained constant. The experiment was repeated three times and the decrease of mRNA enrichment was 30% with a standard deviation of 7% (students' t-test, p<0.05).

FIGS. 5A, 5B, 5C and 5D: EnHD upregulates BPAG1e MRNA and BPAG1e protein levels in keratinocytes expressing Engrailed.
(A) GMA24FIA keratinocytes in culture were stained with a polyclonal anti-Engrailed (aEnhb-1) antibody (right panel without first antibody), Bar=
(B) GMA24FIA cells treated overnight with EnHD (right lane) show a five fold increase of the BPAG1e transcripts, whereas the accumulation of the GAPDH mRNA is not modified.
(C) GMA24FIA cells were incubated overnight with EnHD in the presence of cycloheximid and BPAG1e transcript was detected by means of in situ hybridization. Bar=
(D) First, the cells were treated overnight with cycloheximide plus or minus EnHD, and cycloheximide was removed two hours prior BPAG1e immunostaining (BP patients autoantisera, Dr. C. Prost, Paris).

FIGS. 6A, 6B, 6C and 6D: Engrailed binds to several sites in the BPAG1e promoter in vi tro.

(A) Mobility shift assay of Engrailed proteins produced in E. coli with fragments of the internal promoter/enhancer. The BPAG1e promoter was digested with BstNI, and the end labeled fragments were investigated for binding to En2. Lane 1: control with 2 µl E. coli extract. Lane 2: 2 µl En2, semipurified from an E. coli extract. Two fragments (−810 to −89 and −2226 to −1569, minus strand) exhibit high affinity j,) binding activity.

(B) DNase I footprint analysis of the promoter fragments with purified EnHD. The fragments were end labeled and incubated with EnHD as described as in the experimental methods. The two left most lanes correspond to the fragment −2226 to −1569. The following four lanes correspond to the fragment −810 to −89 with a long run (middle) and a short run (right). The footprints are indicated by black bars. 0 is control without protein and 10 is EnHD (10 µl, 6 ng).

(C) Gel shift analysis of two regions tested in footprinting (underlined in 6D) with full length En2. The gel shifts in the right panels were performed using the oligonucleotide CTCAAATAATTAGTCAT-TAAAAAAAATAAAGGCATATGAGCCAGCCTA (SEQ ID NO:1) and in the left pannel using the oligonucleotpide CGCAGAATATTGGCTCAGTAAC-TAAGTGTG (SEQ ID NO:2). 0, no extract; C E. coli extract; En En2 expressing E. coli extract.

(D) Sequence of the two footprinted regions (SEQ ID NOS 24 and 25) (black boxes) of the BPAG1e promoter. The protected regions are indicated in bold.

Figure 7A:
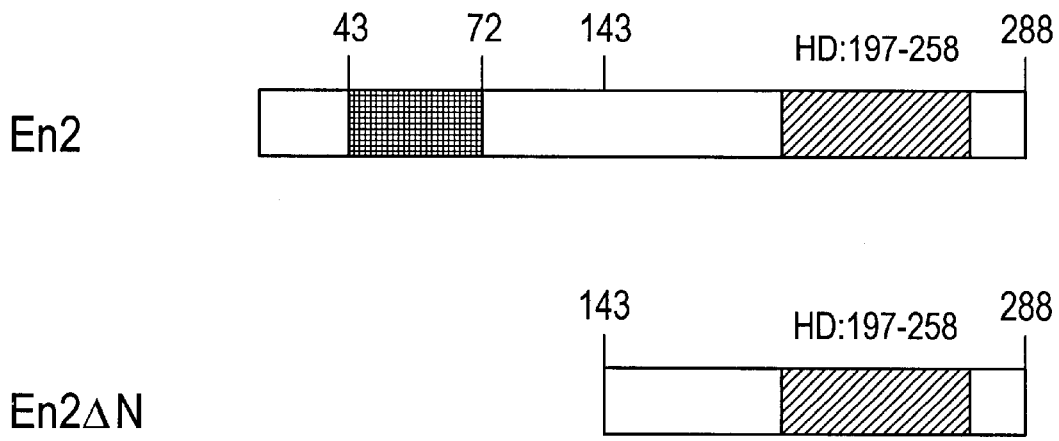
FIG. 7A is a schematic depiction of constructs used for cotransfection.
Figure 7B:
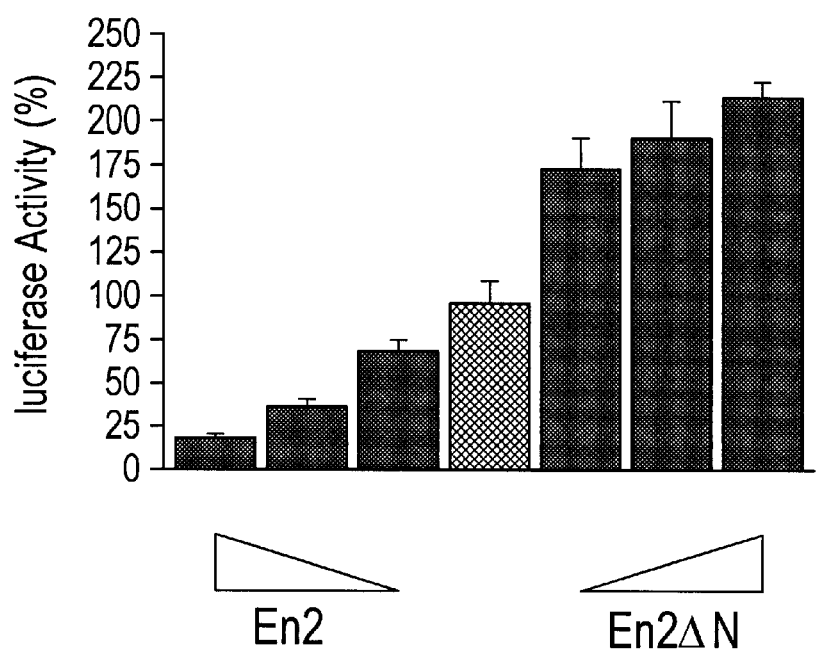
FIG. 7B is a bar graph showing luciferase activity, both as illustrations of the invention.

FIGS. 7A and 7B: Engrailed2 represses and EnHD activates BPAG1e promoter activity.

(A) Schematic depiction of the two constructs used for cotransfection with pBP-luc.

(B) GMA24FIA cells were transfected with pBP-luc alone or with increasing doses of En2 or En2ÆN as noted above. After 48 hours luciferase activity was measured in the cell lysates. Each value corresponds to the average of 4 independent wells. The effects of the two constructs are opposite and dose-dependent.

Figure 8:
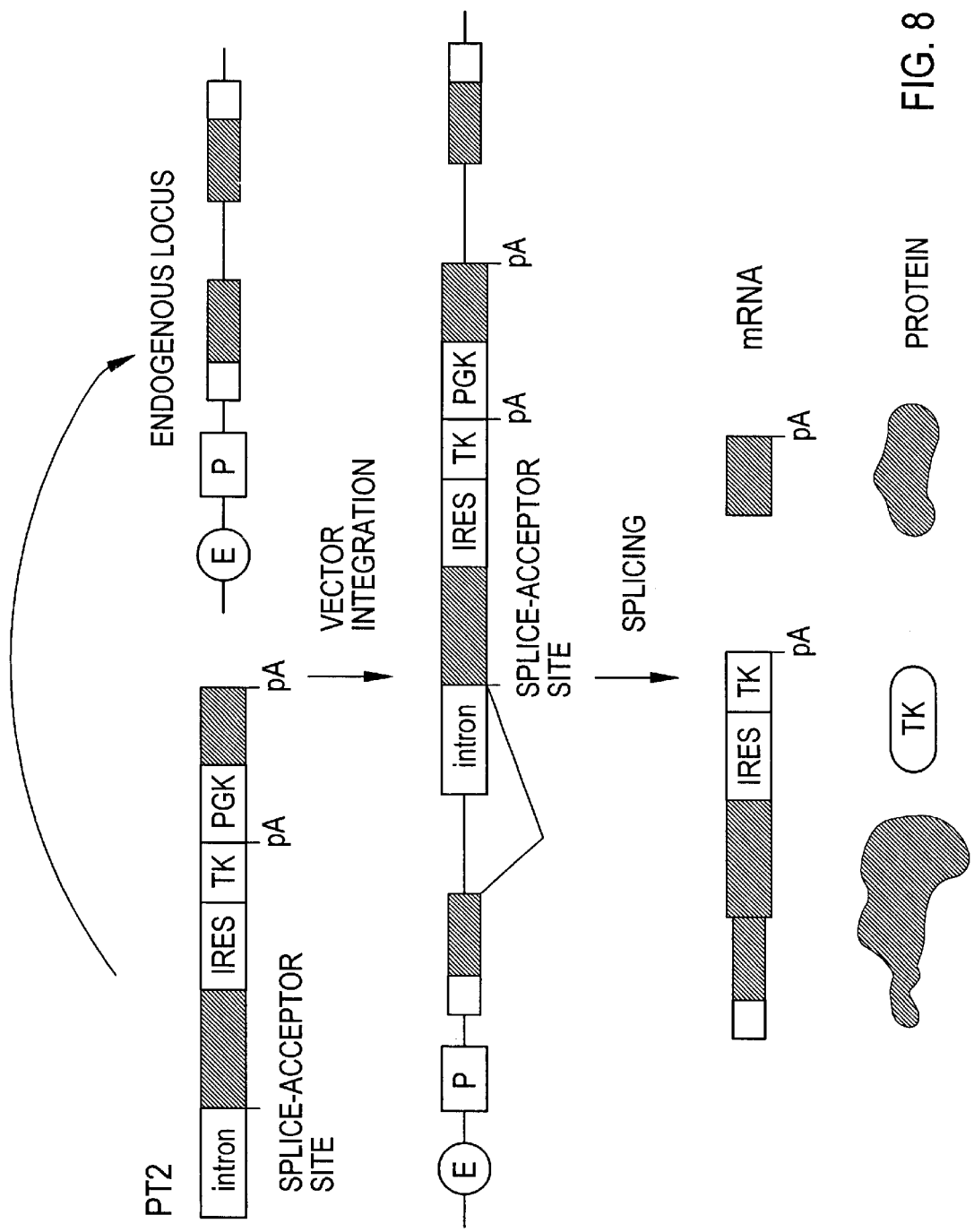
FIG. 8 is an illustration of a vector used in an illustration of this invention.

FIG. 8: Illustration of PT2 vector and its function in the method of the present invention.

Experimental Strategy

Figure 1B:
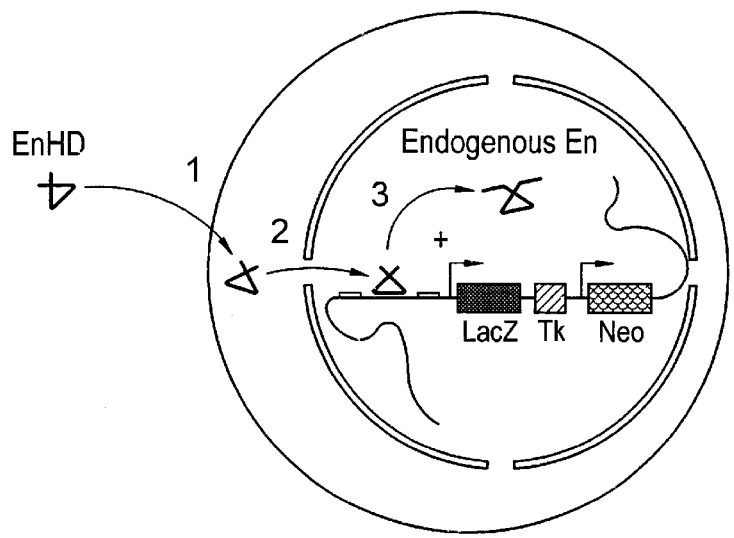
Figure 1C:
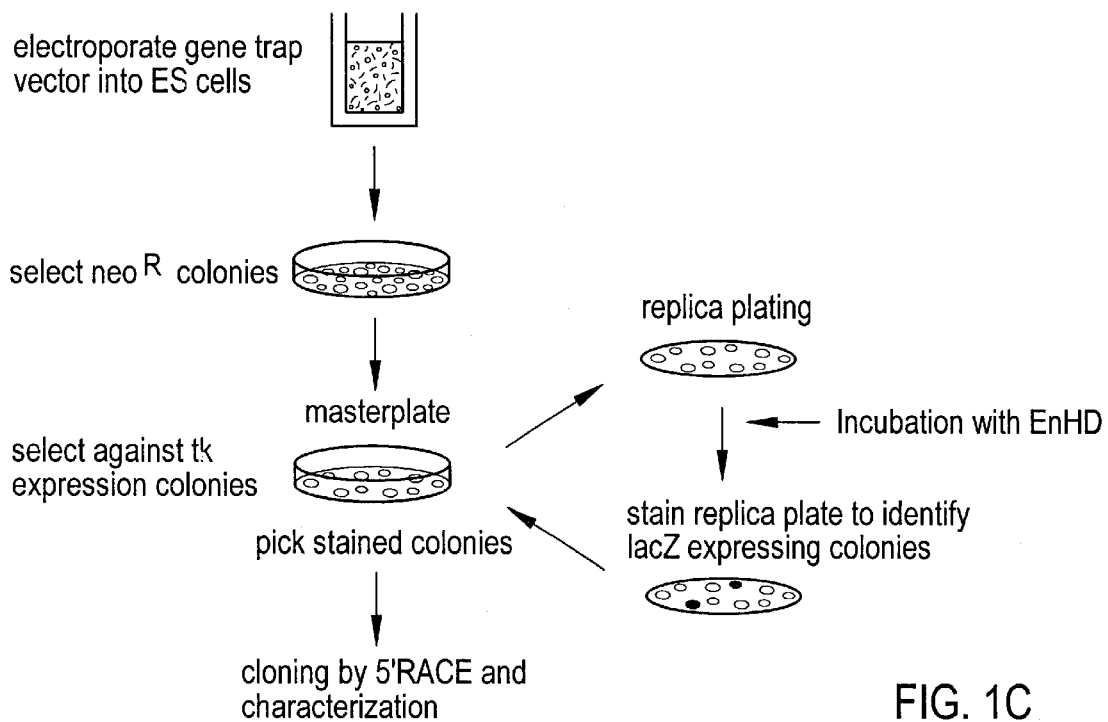

FIG. 1 illustrates the principle of the novel strategy developed according to the present invention. ES cells are electroporated with a linearized PT2 gene trap vector. This vector contains a reporter gene LacZ fused in frame to a splice-acceptor site followed by a thymidine kinase (tk) gene linked to an Internal Ribosomal Entry Site (IRES), thus, a bicistronic message will be made containing lacZ and tk (FIG. 1A). By adding ganciclovir to the medium, clones which express the tk gene can be eliminated, therefore, selecting against integrations into genes which are constitutively active. A second gene coding for neomycin resistance and placed under the control of the phosphoglycerate kinase (PGK) promoter allows for positive selection of transfected clones. The clones are the replicated on polyester filters and incubated with EnHD. Assuming that Engrailed primarily represses transcription via a N-terminal domain missing in EnHD the introduction of EnHD, by competing with endogenous Engrailed, might lift the repression (FIG. 1B). This will lead to the identification of LacZ-expressing clones on the polyester filters and, subsequently, on the master plate. The putative Engrailed targets can then be cloned using 5' RACE-PCR strategies (FIG. 1C). In this scheme (FIG. 1B), we have represented the case, in which LacZ is integrated within a direct Engrailed target. However, LacZ could also be expressed after integration in a gene indirectly regulated by Engrailed (e.g. in its genetic regulation pathway).

In this study, we used the chicken Engrailed homeodomain (EnHD), since specific antibodies are available to distinguish between the avian polypeptide and the endogenous mammalian Engrailed. The high sequence conservation between the different EnHDs and the normal development of a mouse in which En1 was mutated and replaced by En2 suggested that the homeodomain used in this study would, in case of success, allow us to identify both En1 and En2 mammalian targets.

Engrailed Homeodomain is Internalized by Cells in Culture

The protocol described in FIG. 1 requires the EnHD added to the culture medium to be internalized by a large number of ES cells. EnHD was produced in E. coli and purified on heparin sepharose. The purity of EnHD was superior to 80% as estimated by SDS-PAGE analysis and coomassie blue staining (FIG. 2A). To test the binding properties of EnHD, gel shift experiments were performed using a DNA fragment containing six copies of the NP6 site (TCAATTAAAT) (SEQ ID NO:3) known to bind Drosophila Engrailed. As seen in FIG. 2B, four distinct complexes are formed when the amount of EnHD is progressively increased from 10 ng to 100 ng, demonstrating that EnHD binds efficiently to NP6 in vitro.

EnHD was labelled with a fluorescein isothiocyanate (FITC) as described previously and added to ES cells in culture for 2 h at 4° C. FIG. 2C (upper Panels) shows that EnHD is efficiently taken up by ES cells. No staining was observed with FITC alone (upper and right Panel) and confocal sections confirmed that the peptide is actually present inside the cells. Similar results were observed with FITC labelled EnHD and by immunocytochemistry (not shown) in GMA24FIA keratinocytes (FIG. 2C, lower Panles), a cell line that has been used in this study (see below). In summary, we conclude that EnHD is efficiently captured by cells in culture.

Identification of a Putative Engrailed Target Gene

A library of 30,000 independent gene trap vector integrations in ES cells was sreened for responsiveness to Engrailed by adding EnHD to the culture medium following the protocol schematized in FIG. 1, leading to the identification of 20 responding clones. The response of these 20 clones was subsequently repeated in 96 well plates in three independent experiments. Eight of the clones consistently showed an induction of reporter gene expression. FIG. 3A illustrates for clone ES-C3, which is the object of the present experiment, how the number of LacZ expressing cells is increased in a dose-dependent manner by the addition of EnHD.

The fusion transcript generated by the gene trap vector integration in clone ES-C3 was characterized by 5'-RACE. An approximately 225 bp fragment was amplified, cloned and subsequently sequenced. This sequence (FIG. 3B) reveals a hybrid cDNA containing the splice acceptor of the gene trap vector sequence and 101 nucleotides showing 100% identity with a sequence found in the type II neural isoform of dystonin (genebank, ref. gb U25158) also called BPAG1n2 (for Bullous Pemphigoid Antigen neural 2). In this sequence, 45 nucleotides correspond to the 5' end of the exon coding for the C-terminus of the actin binding domain of dystonin and 56 nt to dystonin exon A (FIG. 3C).

The BPAG1n2 and LacZ sequences are in frame allowing the expression of a fusion protein, consistent with the observed β-galactosidase activity. The existence of this hybrid cDNA was confirmed by RT-PCR using two independent sets of PCR primers. To further demonstrate that the hybrid mRNA was present in ES-C3 cells, an RNase protection assay was performed using an antisense RNA probe made from the BPAG1n2-LacZ cDNA and total RNA from ES-C3 cells and normal ES cells. As expected, a 200 nucleotides fragment corresponding to the hybrid mRNA was protected in the ES-C3 cells RNA but not in control RNA (data not shown).

The organization of the dt/BPAG1 locus is described in FIG. 3C. The dt/BPAG1 locus encodes at least three different isoforms coding for BPAG1n1, BPAG1n2 and BPAG1e. The two former isoforms are expressed in the nervous system and the latter in keratinocytes of the epidermal basal layer. The amino terminus of the neural isoforms differs from that of BPAG1e by the presence of a functional actin-binding domain (ABD), while the carboxyl terminus in common with all three isoforms contains an intermediate filament binding domain (IFBD). With respect to the hybrid cDNA sequence, it may be seen, that the gene trap vector most likely integrated into an intron of the ABD region of the dt/BPAG1 locus leading to a truncation of the two neural isoforms (FIG. 3C).

Ex Vivo Regulation of BPAG1n Expression by EnHD

To further investigate the genetic regulation between Engrailed and Dt/BPAG1n, we used neuronal cells which express both genes. Rat pheochromocytoma derived PC12 cells adopt a sympathetic neuron-like phenotype and express Dt/BPAG1n and En1 after addition of nerve growth factor (NGF). Since the homeodomains of En1 and En2 are functionally identical, EnHD should be able to bind to En1 target sites and, thus, to compete with endogenous Engrailed. PC12 cells were incubated three days with NGF and treated overnight with EnHD (300 ng/$10^5$ cells) in the presence of cycloheximide. FIG. 4A represents a Northern blot analysis performed with a dt-ABD probe recognizing the two mRNAs corresponding to the two neural isoforms. The two mRNAs cannot be distinguished on the basis of their size, and a single band of 15 kb was detected with a twofold decrease in mRNA accumulation only 12 hours following addition of EnHD. This decrease quantified by Phosphoimager analysis is not due to a general decrease in MRNA transcription or accumulation since glyceraldehyde-3-phosphate dehydrogenase (GAPDH) expression remained unmodified. The same experiment was reproduced three times and gave identical qualitative results (legend in FIG. 4). Since cycloheximide inhibits translation, the result of the latter experiments suggest that EnHD, in this model, acts directly on the regulation of BPAG1n transcription.

Ex Vivo Regulation of BPAG1e Expression by EnHD

In addition to the overlapping expression patterns of BPAG1n and Engrailed in the CNS we observed that En1 and BPAg1e were also co-expressed in keratinocytes present in the basal layer of the epidermis (not shown). We, therefore, investigated whether in addition to the neuronal BPAG1 isoforms, the epidermal isoform (BPAG1e) was also regulated by Engrailed. For that purpose, we studied the expression of BPAG1e and Engrailed in a human keratinocyte immortalized cell line (GMA24F1A cell line) which behave like basal keratinocytes. αEnhb-1, a polyclonal antibody recognizing both En1 and En2, stains the cell nuclei (FIG. 5A) and recognizes a single 52 kDa protein in Western blot (not shown), demonstrating, that these cells express En1. By performing Northern blot analysis, a single transcript of 9 kb corresponding to BPAG1e mRNA was detected (FIG. 5B), but not the 15 kb transcripts corresponding to the BPAG1n isoforms. Having verified that GMA24FIA cells internalize EnHD (FIG. 2D), we analyzed the effect of homeodomain internalization on BPAG1e expression. As shown in FIG. 5B, the overnight addition of EnHD enhances the content in BPAG1e mRNA by at least a factor of five. The in situ hybridizations of FIG. 5C demonstrate a strong effect of ENHD on the amount of BPAG1e MRNA, even in the presence of cycloheximide suggesting that the regulation is direct. Finally, GMA24FIA cells were incubated overnight with or without EnHD in the presence of cycloheximide, washed and further incubated for 2 h without cycloheximide allowing de novo protein synthesis. As illustrated in FIG. 5D, EnHD had a strong positive effect on BPAG1e synthesis and accumulation under the cell membrane. These data demonstrate that BPAG1e expression is activated by EnHD in GMA24FIA cells.

An Internal Promoter/enhancer of BPAG1 is a Target of Engrgailed Protein

An internal promoter/enhancer has been identified within the BPAG1 locus (see FIG. 6). This internal promoter/enhancer directs the in vivo expression of a lacZ reporter in epidermal keratinocytes, as well as in regions of the CNS which express Engrailed (e.g. midbrain). Therefore, it may act as a regulator of both BPAG1n and BPAG1e isoforms. To localize putative binding sites for Engrailed, within the BPAG1 internal promoter/enhancer, gel shift assays were performed using labeled BstNI restriction endonuclease fragments of the (−2466 to −93) promoter region and partially purified chicken En2 (En2) protein. As seen in FIG. 6A, the two larger fragments (−2226 to −1569) and (−810 to −89) shift in the presence of En2 (arrows) revealing the existence of functional binding sites.

The two fragments were analyzed by DNase I footprinting with EnHD. The footprinting reactions were performed with both labeled strands and gave identical results. Therefore, only the results for one strand are shown for each fragment. The (−810 to −89) and (−2226 to −1569) fragments revealed 5 specific footprints each (FIG. 6B). As seen in FIG. 6D, several of the protected areas (in bold) contain the ATTA consensus core sequence for homeodomain proteins, among these some are almost identical to the NP6 sequence TCAATTAAAT (SEQ ID NO:3), that has been shown to be the target for Engrailed in Drosophila. Two EnHD footprints do not contain any ATTA sequences (FIG. 6D).

To test whether these binding sites for EnHD would also be recognized by full-length Engrailed2, gel shift assays were performed with bacterially produced En2. Two pairs of oligonucleotides corresponding to two different protected areas were used. One (−2225 to −2180) contains three bona fide ATTA motifs while the other (−694 to −665) lacks any ATTA sequence (underlined in FIG. 6D). As seen in FIG. 6C, En2 formed two shifting complexes with both pairs of oligonucleotides, demonstrating, that En2 efficiently binds at least two sequences protected by EnHD in the footprinting analysis, including a sequence without any ATTA core.

BPAG1 Internal Promoter/enhancer Activity is Regulated by En2

The 2.3 kb HindIII/BamHI genomic fragment (position −2463 to −89) of BPAG1e conferring specific expression to reporter genes expressed in keratinocytes and in the CNS was placed in front of the luciferase gene in a pGL2 derived vector (pBP-luc). The reporter gene was co-transfected in GMA24FIA cells with a plasmid coding for full-length En2 or a Plasmid coding for En2 with deleted N-terminal domain (En2ÆN). The latter En2ÆN lacks the domain responsible for mediating active repression and is therefore expected to act like EnHD. The co-transfecting pBP-luc with increasing amounts of En2ÆN results in a dose-dependent increase in promoter activity whereas full-length En2 has the opposite and also dose-dependent effect (FIG. 7). Co-transfection of increasing amounts of either plasmid with a β-galactosidase expressing plasmid demonstrated that the two plasmids had no influence on cell survival (not shown). In summary, we conclude, that En2 directly regulates BPAG1e promoter activity and that, in GMA24FIA cells, En2 and En2ÆN have opposite effects on this activity.

Gene trap technology has been used herein to identify and randomly mutate genes in ES cells. These gene trap integrations can be further screened for specific expression patterns in vivo and in vitro. Now, we have further developed this technology to identify and mutate genes regulated by homeodomain-containing proteins. This novel approach has several advantages over other technologies aimed at identifying differentially expressed genes such as the two-hybrid system and differential display. The tagged target genes can be easily cloned and characterized using PCR strategies. The expression of the trapped target genes can be studied following reporter gene activity in chimeras and F1 progenies, thus allowing to predetermine cell and tissue specific interactions. Reporter gene expression can be used as a helpful marker to dissect the network of genetic interactions. The integrations might result in a mutant phenotype which can be studied after germ line transmission.

To identify rare gene trap vector integrations into genes which are active downstream in specific genetic pathways, the classical screening procedure was improved. To this end a thymidine kinase gene fused to an internal ribosomal entry site (IRES) 3' of the LacZ gene was included into the PT1 gene trap vector. Most integrations into constitutively active genes could thus be eliminated by the addition of ganciclovir to the selection medium. The use of this novel bicistronic vector, in combination with the replica plating technique allowed us to screen a large number of gene trap vector integrations and to specifically identify target genes of exogenously added homeodomain containing transcription factors.

Identification of Engrailed Target Genes by Translocation

The homeodomain of Antennapedia (AntpHD), Hoxa5HD und FtzHD as well as full-length Hoxa-5 and Hoxc-8 is able to penetrate into the cytoplasm and nucleus of living cells in culture. Although the mechanism of translocation across the biological membrane is not fully understood, experiments with several peptide variants derived from the third helix of AntpHD suggest, that translocation does not require a chiral receptor and does not involve classical endocytosis. A distinct advantage of the technique is that the polypetides gain access to the cytoplasm and to the nucleus without being degraded in the endocytosis pathway and find themselves inside an unperturbed environment. This latter point is particularly important in the case of the introduction of full-length homeodomains or homeoproteins which, when in the nuclei, will only bind to sites made accessible by the structure of the chrmomatin. Therefore, the amount of non-specific interactions will be reduced, if not eliminated.

Regulations of BPAG1n Expression by Engrailed

In this study, we identified 8 gene trap vector integrations in ES cells that respond to EnHD when added to the culture medium. In one of the clones, ES-C3, the integration occured into the dt/BPAG1 locus. The integration site of the gene trap vector within an intron of the ABD domain of BPAG1n suggested that BPAG1n is downstream of Engrailed. In situ hybridization demonstrates that BPAG1n is expressed in several domains of the mouse embryonic CNS, including regions, in which Engrailed is not expressed. The expression outside of the Engrailed domains suggests that BPAG1n is also a target for other regulatory proteins, possibly but probably not exclusively other homeoproteins. In fact, due to the ubiquity of the cognate sites for homeoprotein binding, it is expected that similar or even identical promoter regions will be recognized by different homeoproteins and homeodomains.

The in vivo decrease in BPAG1n expression in Engrailed mutants, therefore, confirms that BPAG1n is in the genetic regulation pathway of Engrailed. The latter observation seems to indicate that, in E12.5 embryos, Engrailed behaves like an activator of BPAG1n expression, whereas in ES cells, in keratinocytes and in the dermomyotome, Engrailed behaves like a repressor. This agrees with the function of Drosophila Engrailed, which may be a repressor or an activator depending on the developmental stage and the cellular context considered. In this respect, it is noteworthy that the activity of a LacZ reporter gene driven by the internal BPAG1 promoter/enhancer in the midbrain of E8.5 to E12.5 mice is enhanced by a positive regulation of an Engrailed responsive element in an neuronal Engrailed expressing area.

Regulation of BPAG1e Expression by Engrailed

The dt/BPAG1 locus also encodes BPAG1e, a protein which in keratinocytes links keratin filaments to hemidesmosomes and thus is important.in the maintenance of the structure of the hemidesmosome. The internal promoter/enhancer sequence upstream of BPAG1e contains several putative homeoprotein binding sites. The latter observation, in addition to in situ hybridization studies showing that the level of BPAG1e expression in the epidermis was significantly increased in the absence of Engrailed, suggested a genetic interaction between BPAG1e and Engrailed. Thus, we verified that En1 and BPAG1e are expressed in basal keratinocytes in vivo (not shown) and in the immortalized keratinocyte cell line GMA24FIA. Using this cell line we could demonstrate that the addition of EnHD increases BPAG1e expression and that this increase is also observed in the presence of cycloheximide. As in the case of BPAG1n, these experiments strongly suggest a direct regulation of BPAG1e by Engrailed, but do not totally exclude an effect of EnHD on the stability of the BPAG1e mRNA. It is also noteworthy that the addition of EnHD increases the amount of transcript suggesting that, in the keratinocytes in contrast to what happens in PC12, Engrailed acts as a repressor.

dt/BPAG1 Contains a Promoter/enhancer Sequence Directly Regulated by Engrailed The presence of an internal promoter upstream of BPAG1e was very useful to verify the validity of the approach taken in the present invention to identify putative Engrailed itarget genes. This promoter is of particular interest, since it drives the expression of LacZ in the midbrain suggesting either that BPAG1e is expressed in the CNS or, and not exclusively, that this domain acts as an Engrailed enhancer in the nervous system for the expression of BPAG1n. The latter interpretation is supported by the fact that like BPAG1n, LacZ driven by the internal promoter is upregulated in the Engrailed expressing domain.

Generality of the Approach

According to the invention, it has been shown, that cell permeable peptides may be used for identification of e.g. homeoprotein targets. Furthermore, it is obvious that by linking of polypeptides to the third helix of AntpHD and, thus, by the internalization thereof, the method presented here can now be extended to other proteins for which active domains have been identified, for example, a DNA-binding domain other than the homeodomain. However, so far all polypeptides of lengths of less than 100 amino-acids that we have synthesized and produced enter the cytoplasm of the cells and in most cases to their nucleus. Since the third helix of AntpHD, which may serve as a vector, comprises 16 amino-acids, it is likely, that active domains with a minimal length of 84 amino-acids can be introduced into living cells, thus opening the way to a new and powerful induction gene trap technology.

Above, the present invention was desribed with refference to a specific gene trap vector and the Engrailed 2 protein. It is understood, that the invention is not restricted to said specific embodiment. On the basis of the above application, the person skilled in the art is able to modify said embodiment, without departing from the described invention.

Experimental Procedures

Cell Culture

ES cells were grown in the D3 ES cell growth medium [Wurst and Yoyner, 1993]. Primary cerebellar and metencephalic cultures of rat brain (P0) were prepared as described previously [Joliot, 1991]. PC12 cells were cultured in DMEM/F12 medium containing 10% horse serum (Seromed) and 5% fetal calf serum (GIBCO). PC12 cells used for experiments were incubated for three days with 50 ng/ml NGF (Boehringer). GMA24FIA is a feeder independent subclone of human keratinocyte strain GMA [Barrandon, 1989]. GMA24FIA were grown in normal KGM supplemented with EGF [Rochat, 1994].

Gene Trap

The gene trap procedure is described in detail by [Hill and Wurst, 1993 a, b], but here a brief outline is given: the ES cells were expanded and electroporated with a HindIII linearized PT2 gene trap vector [Wurst, 1993]. Following electroporation cells were plated on gelatin coated 10 mm plates and cultured for 8 days in ES medium containing G418 (200 µg/ml) and 2 mM ganciclovir. After 8 days of selection a polyester membranewas placed on top of the cells, covered with glass beads, medium was added and cells were cultured for additional 48 hours. Then, the polyester filters were removed, rinsed in PBS and placed in a new dish with induction medium containing EnHD (30 ng/$10^4$ cells). After 48 hours the membranes were fixed and stained for β-galactosidase activity as described in Hill and Wurst (1993). β-galactosidase positive clones were picked, expanded and retested in 96 well plates in three independent experiments.

Expression and Purification of ENHD and Chicken Engrailed 2

The 60 amino-acids homeodomain of chicken Engrailed 2(EnHD) protein was isolated from a plasmid containing the chicken cDNA sequence using thefollowing primers: 5'-TTTCATATGGAAGACAAGCGGCCCCIS-3 (SEQ ID NO:4) and 5'-GGGGGATCCCTACGCCTTCTTGATCTTGGCTC3' (SEQ ID NO:5).

The PCR-product was ligated into pBluescript. The construct was then subcloned into the pET-3a expression vector. This plasmid was transformed into BL21(DE3)pLysS and expression of EnHD was induced by addition of 0,8 mM IPTG. The protein was isolated by sonicating the bacteria in buffer A (20 mM HEPES, pH 7.9, 1 mM EDTA, 5 mM $MgCl_2$, 0.2 M NaCl, 0.02 mg/ml DNase I and protease inhibitor: 0.5 mM Pefablock, 10 µg/ml Pepstatin, 10 µg/ml Aprotinin, 1 µg/ml α2-Macroglobulin) followed by a streptomycin sulfate precipitation (20 mg/ml final concentration, Boehringer) and purification using FPLC with a stepwise elution using KCl over a heparin-sepharose column (Pharmacia). Purity was estimated by Coomassie staining after SDS-PAGE analysis, and protein amount determined by the Bradford method (Kit Micro BCA, Pierce). FITC-labelling of EnHD was performed as described previously [Joliot, 1991].

To produce chicken En2 protein, a 1.1 kb EcoRI fragment containing the complete cDNA of En2 was inserted into the EcoRI site of an intermediate vector obtained by inserting the following adaptator oligonucleotides: 5'-AGCTTCATATGGAGGAGGGCGGCCGCAGCCCC CGGGAGGAGGAATTCG-3' (SEQ ID NO:6) and 5'-GATCCGAATTCCTCCTCCCGGGGGCTGCGGCC GCCCTCCTCCATATGA-3 (SEQ ID NO:7) in BamHI and NdeI digested pBluescript. 5' uncoding sequence was removed by digesting with SmaI. The En2 sequence was then inserted into the NdeI and BamHI sites of the expression vector pET-3a.

Chicken Engrailed2 (ChEn2) protein was produced as described for EnHD. A semipurified fraction was obtained by lysing the bacteria and incubating the extract with heparin sepharose according to [Bourbon, 1995]. The heparin binding fraction was then dialyzed,and concentrated (Centriprep, Amicon). ChEn2 was identified by western blot analysis using 4D9 antibody (Patel et al., 1989) and used for gel shift assays.

5'-RACE

Total RNA was isolated from ES-C3 cells using standard procedures (Kit RNAeasy, Quiagen). 200 ng total RNA from ES-C3 cells were reverse transcribed using "Superscript II"reverse transcriptase (Gibzo/BRL) and a primer (5'-TGGCGAAGGGGGATGTGC-3' SEQ ID NO:8) located in the 5' region of the LacZ gene sequences according to the manufacturers's instructions. A tenth of the cDNAwas tailed with dCTPs using terminal transferase (Gibco/BRL). The C-tailed cDNA was amplified by PCR using a primer from the splice-acceptor region of the gene trap vector: 5'-GACTCTGGCGCCGCTGCTCTGTCAG-3' (SEQ ID NO:9) and a poly-G primer: 5'-CUACUACUACUAGGCCACGCGTCGACTAGTAC GGIGGGIIGGGIIG-3' (SEQ ID NO:10).

1 µl of the 50 ml PCR reaction was then used in a second PCR reaction using a nested primer fromthe splice-acceptor region: (5'-ACCTGTTGGTCTGAAACTCAGCCT3' SEQ ID NO:11) and a primer: (5'-CUACUACUACUAGGCCACGCGTCGACTAGTAC-3'

SEQ ID NO:12) recognizing the 5' part of the poly G primer. The cDNA fragments were cloned into the pAMP plasmid (GIBCO/BRL) and purified. To verify the existence of the fusion transcript, 400 ng total RNA from ES-C3 cells were reverse transcribed using random hexamer primers. A first round of PCR was performed using an upstream primer from the BPAG1n2 sequence (5'-TGCTGGACCCAGCCGAGAGGGCTGTGC-3' SEQ ID NO:13) and a LacZ primer (51-TGGCGAAAGGGGGATGTGCTGCAAGGCG-3' SEQ ID NO:14) and a second round of PCR reaction was performed using nested primers (5'-AGCAGATGAGCGGGACAAAGTTCAAAAG3' SEQ ID NO:15) and (5'-CGCCAGGGTTTTCCCAGTCACGACGTTG-3' SEQ ID NO:16). The fragment was isolated, cloned into pBluescript and sequenced.

Northern Blot Analysis and in Situ Hybridization

Cells were treated overnight with ENHD (300 ng/$10^5$ cells) in presence or in absence of cyclohexmide $10^{-6}$M. Northern Blot and in situ hybridization were performed using standard techniques [Ausubel, 1994]. Glyceraldehyde-3-phosphate-dehydrogenase (GAPDH) served as a loading control. Northern blots were quantified with a phosphoimager. To detect the BPAG1e transcript in keratinocytes, a probe was isolated from GMA24FIA cDNA by polymerase chain reaction (PCR), using Taq polymerase and the following oligonucleotide primer 5'-GGAAGTTCTTCCTCTACT-3'(SEQ ID NO:17) and 5'-GGTTGAAACTACTCAGAG-3'. The resulting 519 bp amplified DNA product extends from position 3048 to position 3567 according to [Tamai, 1993]. This PCR product was blunt ended using Klenow enzyme and cloned into the EcoRV site of pBluescript. BPAG1n isoforms were detected using a 664 bp DNA fragment corresponding to the "dt-ABD" probe which hybridizes to the actin binding domain [Bernier, 1995].

Transfection Assays

To express luciferase under control of BPAG1e promoter, a 7 kb SacI/SalI fragment derived from the genomic lambda zap clone (mdt 1.4.I.2, kindly provided by Dr. R. Kothary) was subcloned into pBluescript (Stratagene). This fragment contained the whole intergenic region as determined by double hybridization with BPAG1e and ABD-dt probes (not shown). A 6,5 kb BamHI fragment was then inserted into the BglII site of pGL2bas (Promega). Finally, a 2.3 kb HindIII fragment was transfered into the HindIII site of pGL2bas leading to pBP-luc. pBP-luc was cotransfected in GMA-48 with pTLlEn2 or pLT1En2ÆNter. Cotransfection assays were performed in suspension with calcium phosphate precipitate as described in [Le Roux, 1995]. Each condition was accomplished in quadruplicate.

Gelshift and DNase I Footprinting

DNA fragments were end labeled by polynucleotide kinase and ($\gamma^{32}$P)ATP. Extracts from *E. coli* expressing EnHD or En2 protein and control *E. coli* extracts were added to the labelled probes in 20 mM Tris-HCl, pH 7.9, 35 mM KCl, 2.5 mM $MgCl_2$, 1 µg poly-dIdC and 15% glycerol, incubated for 10 min on ice and then analyzed on native 6% polyacrylamide gels.

For DNase I footprints, the promoter fragments were end labeled using Klenow enzyme. Foot printing assays were performed by incubating 200 ng fragment with EnHD in a final volume of 50 µl incubation mixture 20 mM Tris-HCl pH 7.9, 35 mM KCl, 2.5 mM $MgCl_2$, 1 µg poly-dIdC, 4% polyvinyl-alcohol and 15% glycerol, for 10 min on ice and then, an equal volume of DNase I in 10 mM $MgCl_2$, 4 mM $CaCl_2$, was added. After 2 min of incubation the reaction was stopped by the addition of an equal volume of stop buffer [Ausubel, 1994], the DNA extracted with phenol and chloroform, ethanol precipitated and analyzed on a 6% sequencing gel. Sequences of oligonucleotide for gel shifts: (5'-GAAAAAGTAATTGAACATTTTTCC-3', upper strand) Sequences of the oligonucleotides used in gel shift assay corresponding to two protected areas in footprininq: (5-GGCTGGCTCATATGCCTTTATTTTTTTTAATGAC TAATTATTTGAG-3' (SEQ ID NO:19), -2222 to -2176, upper strand) and by 6 0) (5'-CACACTTAGTTACTGAGCCAATATTCTGCG-3' (SEQ ID NO:20) -695 to -664, upper strand).

What is claimed is:

1. A method for the identification of a member that interacts with a transcription factor, said member selected from the group consisting of transcription factor responsive elements and target genes, said method comprising the steps of:
   (a) introducing a gene trap vector into an eukaryotic cell in culture, wherein the gene trap vector comprises the following elements in functional arrangement:
      a reporter gene,
      a polyadenylation site, and
      a selectable marker gene, thereby integrating said gene trap vector into the genome of said eukaryotic cell;
   (b) selecting cells containing said gene trap vector so integrated;
   (c) contacting said cells so selected with said transcription factor by adding said transcription factor to a cell culture medium of said cells so selected, wherein said transcription factor contains or is attached to a polypeptide comprising a third helix of a homeodomain capable of crossing the cell membrane and reaching the nucleus;
   (d) of the cells contacted in step (c), identifying and cultivating those having a target gene into which said gene trap vector has integrated and whose reporter gene activity has been altered as a result of the interaction of said transcription factor with a transcription factor responsive element of said target gene;
   (e) identifying said target gene; and
   (f) identifying the transcription factor responsive elements in the sequence adjacent to or within said target gene by detecting specific interaction between the transcription factor responsive elements and the transcription factor.

2. A method according to claim 1, in which step (a) is performed by a member selected from the group consisting of electroporation, transfection, lipofection, and a retroviral vectorl.

3. A method according to claim 1, in which the expression of said reporter gene is detectable in eukaryotic cells.

4. A method according to claim 1, in which said gene trap vector comprises a promoter for said selectable marker gene.

5. A method according to claim 1, in which said gene trap vector comprises a phosphoglycerate kinase (PGK) promoter for said selection marker gene that is active in the embryonic stem cells ES-C3.

6. A method according to claim 1, in which said selectable marker gene is an antibiotic resistance marker gene.

7. A method according to claim 1, in which said reporter gene is a member selected from the group consisting of thymidine kinase gene, diphtheria gene, and HAT gene to select against integrations in constitutively active genes.

8. A method according to claim 1, in which step (b) is performed by exposing said cells so integrated to a selection agent that is specific for said selectable marker gene.

9. A method according to claim 8, in which said selection agent is an antibiotic.

10. A method according to claim 1, in which said transcription factor is one that is coded by a gene selected from the group consisting of zinc finger genes, Pou genes, homeobox containing genes, HGM-box containing genes and winged helix genes, wherein said transcription factor contains or is attached to a polypeptide comprising a third helix of a homeodomain capable of crossing the cell membrane and reaching the nucleus.

11. A method according to claim 1, in which said eukaryotic cell is a member selected from the group consisting of a fibroblast cell, a neuronal cell, a tumor cell, and a yeast cell.

12. A method according to claim 1, in which said polypeptide is a third helix of a homeodomain.

13. A method according to claim 1, in which said polypeptide is a homeodomain.

14. A method according to claim 1, in which the homeodomain is from a homeoprotein selected from the group consisting of: Engrailed-1, Engrailed-2, Antennapedia, Hoxa-5, Ftz, and Hoxc-8.

15. A method for the identification of a member that interacts with a transcription factor, said member selected from the group consisting of transcription factor responsive elements and target genes, said method comprising the steps of:
   (a) introducing a gene trap vector into an eukaryotic cell in culture, wherein the gene trap vector comprises the following elements in fumctional arrangement:
      a reporter gene,
      a polyadenylation site, and
      a selectable marker gene, thereby integrating said gene trap vector into the genome of said eukaryotic cell;
   (b) selecting cells containing said gene trap vector so integrated;
   (c) contacting said cells so selected with said transcription factor by adding said transcription factor to a cell culture medium of said cells so selected, wherein said transcription factor contains a homeodomain to cross the cell membrane and reach the nucleus;
   (d) of the cells contacted in step (c), identifying and cultivating those having a target gene into which said gene trap vector has integrated and whose reporter gene activity has been altered as a result of the interaction of said transcription factor with a transcription factor responsive element of said target gene;
   (e) identifying said target gene; and
   (f) identifying the transcription factor responsive elements in the sequence adjacent to or within said target gene by detecting specific interaction between the transcription factor responsive elements and the transcription factor.

* * * * *

SEQUENCE LISTING

```
<160> NUMBER OF SEQ ID NOS: 25

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence:
      oligonucleotide used in gelshift analysis footprinting in right
      panel of Figure 6C

<400> SEQUENCE: 1
ctcaaataat tagtcattaa aaaaaataaa ggcatatgag ccagcct                47

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:
``` oligonucleotide used in gelshift analysis footprinting in left
panel of Figure 6C

<400> SEQUENCE: 2
cgcagaatat tggctcagta actaagtgtg                              30

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence:NP6 site

<400> SEQUENCE: 3
tcaattaaat                                                   10

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:primer for
    isolation of 60 amino acid homeodomain of chicken
    Engrailed 2 (EnHD) protein from plasmid containing
    chicken cDNA sequence

<400> SEQUENCE: 4
tttcatatgg aagacaagcg gccccg                                 26

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence:primer for
    isolation of 60 amino acid homeodomain of chicken
    Engrailed 2 (EnHD) protein from plasmid containing
    chicken cDNA sequence

<400> SEQUENCE: 5
gggggatccc tacgccttct tgatcttggc tc                          32

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence:adaptor
    oligonucleotide

<400> SEQUENCE: 6
agcttcatat ggaggagggc ggccgcagcc cccgggagga ggaattcg          48

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence:adaptor
    oligonucleotide

<400> SEQUENCE: 7
gatccgaatt cctcctcccg ggggctgcgg ccgccctcct ccatatga          48

<210> SEQ ID NO 8
<211> LENGTH: 18
<212> TYPE: DNA

```
<213> ORGANISM: Artificial Sequence
<220> FEATURE:
<223> OTHER INFORMATION: Description of Artificial Sequence:primer
      located in the 5' region of LacZ gene sequences

<400> SEQUENCE: 8
tggcgaaggg ggatgtgc                                                         18

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:primer from
      the splice-acceptor region of the gene trap vector

<400> SEQUENCE: 9
gactctggcg ccgctgctct gtcag                                                 25

<210> SEQ ID NO 10
<211> LENGTH: 46
<212> TYPE: DNA/RNA
<213> ORGANISM: Artificial Sequence
<220> FEATURE:
<223> OTHER INFORMATION: Description of Combined DNA/RNA Molecule:poly-G
      primer
<223> OTHER INFORMATION: Description of Artificial Sequence:poly-G
      primer
<221> NAME/KEY: modified_base
<222> LOCATION: (35)
<223> OTHER INFORMATION: n = i
<221> NAME/KEY: modified_base
<222> LOCATION: (39)
<223> OTHER INFORMATION: n = i
<221> NAME/KEY: modified_base
<222> LOCATION: (40)
<223> OTHER INFORMATION: n = i
<221> NAME/KEY: modified_base
<222> LOCATION: (44)
<223> OTHER INFORMATION: n = i
<221> NAME/KEY: modified_base
<222> LOCATION: (45)
<223> OTHER INFORMATION: n = i

<400> SEQUENCE: 10
cuacuacuac uaggccacgc gtcgactagt acggngggnn gggnng                          46

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:nested
      primer from the splice-acceptor region

<400> SEQUENCE: 11
acctgttggt ctgaaactca gcct                                                  24

<210> SEQ ID NO 12
<211> LENGTH: 32
<212> TYPE: DNA/RNA
<213> ORGANISM: Artificial Sequence
<220> FEATURE:
<223> OTHER INFORMATION: Description of Combined DNA/RNA Molecule:primer
      recognizing the 5' part of the poly-G primer
<223> OTHER INFORMATION: Description of Artificial Sequence:primer
      recognizing the 5' part of the poly-G primer

<400> SEQUENCE: 12
cuacuacuac uaggccacgc gtcgactagt ac                                         32
```

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:upstream
    primer from the BPAGln2 sequence

<400> SEQUENCE: 13
tgctggaccc agccgagagg gctgtgc                                    27

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence:LacZ primer

<400> SEQUENCE: 14
tggcgaaagg gggatgtgct gcaaggcg                                   28

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence:nested
    primer for second round of PCR

<400> SEQUENCE: 15
agcagatgag cgggacaaag ttcaaaag                                   28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence:nested
    primer for second round of PCR

<400> SEQUENCE: 16
cgccagggtt ttcccagtca cgacgttg                                   28

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:
    oligonucleotide primer for probe isolation from GMA24FIA cDNA

<400> SEQUENCE: 17
ggaagttctt cctctact                                              18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:
    oligonucleotide primer for probe isolation from GMA24FIA cDNA

<400> SEQUENCE: 18
ggttgaaact actcagag                                              18

```
<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:upper strand
      oligonucleotide for gelshifts

<400> SEQUENCE: 19
gaaaaagtaa ttgaacattt ttcc                                                 24

<210> SEQ ID NO 20
<211> LENGTH: 46
<212> TYPE: DNA
<213> ORGANISM: Artificial Sequence
<220> FEATURE:
<223> OTHER INFORMATION: Description of Artificial Sequence:-2222 to
      -2176, upper strand oligonucleotide used in gel shift
      assay corresponding to protected area in
      footprinting

<400> SEQUENCE: 20
ggctggctca tatgccttta ttttttttaa tgactaatta tttgag                         46

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:-695 to
      -664, Upper strand oligonucleotide used in gel shift
      assay corresponding to protected area in
      footprinting

<400> SEQUENCE: 21
cacacttagt tactgagcca atattctgcg                                           30

<210> SEQ ID NO 22
<211> LENGTH: 225
<212> TYPE: DNA
<213> ORGANISM: Artificial Sequence
<220> FEATURE:
<223> OTHER INFORMATION: Description of Artificial Sequence:BPAGln2-
      EnLacZ hybrid cDNA revealed by 5' RACE of ES-C3 mRNA
<221> NAME/KEY: CDS
<222> LOCATION: (3)..(218)
<223> OTHER INFORMATION: deduced fusion protein

<400> SEQUENCE: 22 tg ctg gac cca gcc gag agg gct gtg ctt cgg ata gca gat gag cgg             47
   Leu Asp Pro Ala Glu Arg Ala Val Leu Arg Ile Ala Asp Glu Arg
    1               5                  10                  15 gac aaa gtt caa aag aaa aca ttt aca aaa tgg ata aat cag cat ctc            95
Asp Lys Val Gln Lys Lys Thr Phe Thr Lys Trp Ile Asn Gln His Leu
             20                  25                  30 atg aag ggt ccc agg tcc cga aaa cca aag aag aag aac cct aac aaa           143
Met Lys Gly Pro Arg Ser Arg Lys Pro Lys Lys Lys Asn Pro Asn Lys
         35                  40                  45 gag gac aag cgg cct cgc aca gcc ttc act gct gag cag ctc cag agg           191
Glu Asp Lys Arg Pro Arg Thr Ala Phe Thr Ala Glu Gln Leu Gln Arg
     50                  55                  60 ctc aag gct gag ttt cag acc aac agg tcgacaa                               225
Leu Lys Ala Glu Phe Gln Thr Asn Arg
 65                  70

<210> SEQ ID NO 23
<211> LENGTH: 72
```

```
<212> TYPE: PRT
<213> ORGANISM: Artificial Sequence
<220> FEATURE:
<223> OTHER INFORMATION: Description of Artificial Sequence:deduced
      fusion

<400> SEQUENCE: 23

Leu Asp Pro Ala Glu Arg Ala Val Leu Arg Ile Ala Asp Glu Arg Asp
 1               5                  10                  15

Lys Val Gln Lys Lys Thr Phe Thr Lys Trp Ile Asn Gln His Leu Met
            20                  25                  30

Lys Gly Pro Arg Ser Arg Lys Pro Lys Lys Asn Pro Asn Lys Glu
        35                  40                  45

Asp Lys Arg Pro Arg Thr Ala Phe Thr Ala Glu Gln Leu Gln Arg Leu
    50                  55                  60

Lys Ala Glu Phe Gln Thr Asn Arg
65                  70

<210> SEQ ID NO 24
<211> LENGTH: 657
<212> TYPE: DNA
<213> ORGANISM: Artificial Sequence
<220> FEATURE:
<223> OTHER INFORMATION: Description of Artificial Sequence:footprinted
      region of BPAG1e promoter

<400> SEQUENCE: 24
ctgaattgca acctgccctg cccttgttt  agcttcccaa gtactgggct tacagtagac     60
ttgcactgta acacaagcct agataataaa cttcttttgt gatatgtatg cagtctgtaa    120
caatacaaag tggattatga tgcacattaa aattctgata ctgctgtagt gaccaaaact    180
atcttttctt ggtgtcttta attcaaatgg ctcatttaat gcttcatttt aactacctgt    240
aagggctgca ccctaagcat ttacagttca ttttagttca taggctgctt atgtagacat    300
ggtaacttta tgagttaaca aggatgcagc cagtaataaa gggtggactt gcctttgcat    360
tcataatgta atatattatc tttaattcat tactccatgg caacactgaa gtcggtgtct    420
aagacagtga ggacacagct acactgcgtg tctctgtttt gtgcttggca ttgagcaaag    480
gcactggtaa gggacccaaa atgatagctc ctctctacat tctcagagcg gatacctaag    540
taacaagtgg cttaaacact ccatgaagaa atatgaaatt ataaccaagg aaagaaccct    600
gaacaatact caaataatta gtcattaaaa aaataaagg catatgagcc agcctgg       657

<210> SEQ ID NO 25
<211> LENGTH: 639
<212> TYPE: DNA
<213> ORGANISM: Artificial Sequence
<220> FEATURE:
<223> OTHER INFORMATION: Description of Artificial Sequence:footprinted
      region of BPAG1e promoter

<400> SEQUENCE: 25
cttaaatatg ctgtggcgtg atatgcaatg cactgcaaat actatgctga taactattct     60
aaagaatcct gcctacagcc attcatttgc ttgctgaggt ttgccttttg tagccagcat    120
taaagccctg caagtacggg cagagcagga cgattgggcg tcactgggaa agatatgcca    180
aatattttca ccaagagtca tccagcttca accacctaaa aacaactca  ggtacacagg    240 agcccgggca gcaccagtga aggtaatgct atcaatacca agcaccaacc agaaacacaa    300
agctcagatc acacagctgg acaaatgctg gacagcaagc agatcccacg tgcttcctaa    360
```

```
cacaaggtaa aatgctggac taatcaataa gtcaataatc aataagcaag cacacaaatt    420
taatgagaaa ccaaatctgt ttccatttga ccatctcttc cattgttcac cgcattaaat    480
taactggaaa aatgttcaat tactttttct ttgtgtgata aactctctct cctaagccac    540
tactgtttgg attctaaaag ccaaagactc cacgcagaat attggctcag taactaagtg    600
tgaatgtgtc tgggcttgct tcttcttcac acagactag                           639
```